United States Patent [19]
Sugata et al.

[11] Patent Number: 5,389,544
[45] Date of Patent: Feb. 14, 1995

[54] METHOD FOR COUNTING LIVING CELLS OF MICROBES AND APPARATUS THEREFOR

[75] Inventors: Kiyoshi Sugata; Ryohei Ueda; Takashi Doi; Takashi Onishi; Kazunori Matsumoto, all of Yokohama, Japan

[73] Assignee: Mitsubishi Jukogyo Kabushiki Kaisha, Tokyo, Japan

[21] Appl. No.: 658,646

[22] Filed: Feb. 21, 1991

[30] Foreign Application Priority Data

Feb. 21, 1990 [JP] Japan .................................. 2-38372
Nov. 6, 1990 [JP] Japan .................................. 2-299056

[51] Int. Cl.⁶ .................. C12M 1/34; C12M 1/00; G01N 21/00
[52] U.S. Cl. ................... 435/291; 435/29; 435/808; 436/52; 436/800; 250/458.1; 250/461.2; 359/196; 359/197; 359/232; 356/213
[58] Field of Search ............ 435/29, 291, 808; 436/52, 800; 250/461.2, 458.1; 356/213; 359/196, 197, 232

[56] References Cited

U.S. PATENT DOCUMENTS 3,657,537  4/1972  Wheeless, Jr. et al. .......... 250/71 R
4,698,308  10/1987  Ikeda .................................. 435/291

FOREIGN PATENT DOCUMENTS 333560  9/1989  European Pat. Off.
61-186854  8/1986  Japan.
61-21084  11/1986  Japan.

OTHER PUBLICATIONS

Shechter, et al. FEBS Letters. vol. 139 No. 1 pp. 121-124 (1982).
Haugland, R. Handbook of Fluorescent Probes and Research Chemicals. Molecular Probes, Eugene, Oreg. (1989) pp. 105-113.
"Review of Scientific Instruments", J. A. Steinkamp, vol. 55, No. 9 pp. 1375-1400.

Primary Examiner—Michael G. Wityshyn
Assistant Examiner—Jane A. Williams
Attorney, Agent, or Firm—Jacobson, Price, Holman & Stern

[57] ABSTRACT

A method for counting living cells of microbes in a fluid sample continuously while flowing the sample using an apparatus which comprises a system for supplying at a predetermined rate to the flow line of the sample a reagent, such as, a derivative of fluorescein, capable of reacting with one or more substances intrinsic of the living cell, such as enzyme, to form an accumulative fluorescent product within the living cells; a reactor inserted in the flow line of the sample and being provided for the reaction of the reagent with the cell-intrinsic substance in the living cells; a photometric detection system arranged subsequent to the reactor for detecting fluorescence emitted as individual luminous point from the fluorescent product in each of the living cells floating in the flowing sample upon irradiation of the fluorescent product by an exciting ray; and an electronic unit including a pulse counter for counting electric pulses produced from each fluorescence from the luminous point.

2 Claims, 3 Drawing Sheets

METHOD FOR COUNTING LIVING CELLS OF MICROBES AND APPARATUS THEREFOR

FIELD OF THE INVENTION AND RELATED ART STATEMENT

The present invention relates to a method for counting living cells of microbes and an apparatus therefor, applicable especially to quality control, assessment of bactericidal effect and so on of raw materials and products of manufacture in food manufacturing plants, medical and pharmaceutical production plants.

A conventional method for counting living cells of microbes most widely employed today is a so-called "agar culture method" in which an amount of sample, of which the number of microbes are to be counted, is admixed with an agar solution prepared with nutrients for the microbe to form a uniform dispersion and the resulting agar medium is cooled and solidified and is included for cultivation for developing colonies of cells multiplicated from each original living cell and the numbers of these colonies are counted under microscope. This method requires a cultivation operation which takes too much time, usually from one to several days, and is inapplicable to real time assessment or control of product quality, bactericidal effect and so on.

For avoiding such a disadvantage, attempts have been made for achieving counting of living cells within a short period of time. For example, there have been proposed, as a technique of indirect determination of the concentration or population of living cells in a sample, (1) a method in which luciferin is reacted, in the presence of luciterase, with adenosine triphosphate (ATP) existing in the living cells to cause emission of luminescence and the intensity of this luminescence is measured and (2) a method in which a derivative of unbelliferone is added to the sample to cause reaction of the unbelliferone derivative with the hydrolases existing in the living cells to liberate unbelliferone and the fluorescence emitted from the liberated unbelliferone upon UV irradiation of the sample is measured.

In the ATP-luciferone method, the reaction of luciferone with ATP is attained after releasing the ATP out of the cell by a heat treatment or with the aid of a surfactant and the cell population is derived from the total luminescence as an analogue value, so that a strict digital determination of the actual numbers of existing individual living cells is not allowed. The apparatus to be used for realizing the ATP-luciferone method is also not designed to allow such determination of the numbers of individual living cells through luminescence measurement. Such a circumstance applies also to the unbelliferone method.

One of the greatest problems for the prior art real time determination of living cell population by the ATP-luciferone method and unbelliferone method was that the technique is only applicable for samples with high population or concentration of the living cells. If the sample to be examined has a living cell concentration not exceeding over $10^4$ per milliliter, the photometric determination of luminescence is difficult due to its most low luminescence level. It is impossible to detect a cell population of, for example, several cells per milliliter of sample by the prior art methods and it is necessary, in such a case, to incorporate a controlled cultural multiplication or a centrifugal "thickening of the cell concentration up to a value permissible of detecting the luminescence by the existing photosensor. In addition, these prior methods do not allow continuous determination of living cell population, so that it was impossible to utilize these prior methods of cell concentration determination for a real time control of processes of, such as, fermentation, pasteurization and so on.

OBJECT AND SUMMARY OF THE INVENTION

The object of the present invention is to provide a method and apparatus permitting real time counting of the individual living cells of microbes in a sample within a brief time.

For such a purpose, the inventors searched for a substance capable of being employed for detecting individual living cells of microbes in a photochemical way among a wide variety of chemical substances and found after many experiments that certain derivatives of fluorescein can be used as detector of living cells.

These fluorescein derivatives themselves produce no fluorescence, but will form a corresponding fluorescent hydrolysis product upon reaction with certain enzymes present in the living cells. This product is retained within the living cells and will accumulate therein without being emitted therefrom, as contrasted to the behavior of unbelliferone mentioned above. Thus, each living cell will emit a fluorescence upon irradiation with a light adapted to excite the fluorescent hydrolysis product, so that the living cells can be counted as individual luminous points.

Basing upon the above fundamental research, the inventors continued their research and confirmed that counting of living cells of microbes in a sample within a brief time was attainable even at a low population of living cells, by a method, which comprises exposing the living cells to a certain derivative of fluorescein to cause it to react with corresponding enzymes present in the living cell to form a fluorescent product within the living cell which is retained and accumulated in the living cell without being emitted therefrom, irradiating the so treated living cells with a light adapted to induce excitation of the fluorescent product and cause emission of the corresponding fluorescence, and counting up the individual living cells each as a luminous point due to such fluorescence.

Thus, according to the first aspect of the present invention, there is provided a method for counting living cells of microbes in a sample, which comprises adding to the sample a reagent capable of reacting with one or more substances intrinsic to the living cell to form an accumulative fluorescent product within the living cell, passing the so treated sample through a photometric detection cell continuously while irradiating the sample with a light having a wave length adapted to induce excitation of the fluorescent product accumulated within each of the living cells to cause emission of corresponding fluorescence from each of the living cells as each individual luminous point and counting up the individual luminous points appearing within an detection area of the detection cell in a certain time interval.

According to the second aspect of the present invention, there is provided an apparatus for counting living cells of microbes in a fluid sample continuously while flowing the sample, which comprises a system for supplying at a predetermined rate to the flow line of the sample a reagent capable of reacting with one or more substances intrinsic to the living cell to form an accumulative fluorescent product within the living cells; a reactor inserted in said flow line of the sample and being provided for said reaction of the reagent with the cell-intrinsic substance in the living cells; and a photometric detection system arranged subsequent to said reactor for detecting fluorescence emitted from the fluorescent product in each of the living cells floating in the flowing sample, said photometric detection system comprising a photometric detection cell having a flat throttled portion to be served for the optical inspection of the sample flowing therethrough defining internally a rectangular thin flow section extending laterally to the flow of the sample, an irradiation means having a light source for irradiating the sample by a light from the light source having a wave length adapted to induce excitation of the fluorescent product accumulated in each of the living cells from each living microbe cell to cause emission of corresponding fluorescence as each individual luminous point, an optoelectronic unit for detecting each of the luminous points with a means for converting the incidental fluorescence into an electric pulse, and an electronic unit for counting the electric pulses and controlling the operation of the apparatus, said optoelectronic unit including an optical inlet aperture in a form of a slit extending parallel to said portion of the photometric detection cell over the entire width of said thin flow section thereof for receiving the fluorescence from each of the individual luminous points in the flowing sample, photosensors disposed in a row parallel to said inlet slit and connected each to each corresponding input terminal of said electronic unit and a condenser lens disposed so as to focus each image of the luminous point onto said row of the photosensors.

By adding a non-fluorescent derivative of fluorescein, for example, fluorescein diacetate, to the fluid sample to be examined for the existing microbial cell population at a predetermined temperature for a predetermined period of time, it reacts with the corresponding hydrolase present in the living microbe cells to form fluorescein which accumulates in the living cells and which is fluorescent and emits fluorescence upon irradiation with an exciting light having an wave length suitable to cause excitation of fluorescein. Thus, each living cell treated by the derivative of fluorescein emits fluorescence upon irradiation of a suitable light, such as an UV light, and appears to the sight as a luminous point. The present invention counts up these luminous points within a certain detection area.

Here, however, it is necessary to use a greater amount of sample, for example, at least 1 ml and preferably more than 10 ml for reliable analytical data, in the case of a low population sample having a living cell population of several cells per milliliter. For a sample with an even lower population, a greater amount of sample is needed.

The present invention provides therefore for realizing a continuous counting of the living cells by flowing the sample through a transparent photometric detection cell while irradiating the cell with a light for exciting fluorescein and detecting the living cells floating in the flow of sample as individual luminous points appearing by the fluorescence from the fluorescein accumulated in the living cells. Here, a very important factor for realizing this technique is a design of the transparent detection cell. It is necessary to choose a thickness of the detection cell as thin as possible, in order to detect each living microbe as a quite small luminous point, since a thicker detection cell will permit a variable image distance for each luminous spot depending on its departure from the cell wall, resulting in a vague image of the luminous spots which may cause a faulty counting result.

In order to enable to deal with a large amount of sample with better accuracy, the photometric detection cell may preferably have a flat throttled portion to serve as the optical inspection of the sample flowing therethrough, defining internally a rectangular thin flow section extending laterally to the flow of the sample. Parallel to this flat portion of the photometric detection cell, an optical inlet aperture in a form of a slit extending over the entire width of said thin flow section thereof is arranged for receiving the fluorescence from each of the individual luminous points in the flowing sample. The sample is irradiated in this flat throttled portion at the position where the optical inlet slit is disposed, by an exciting light laterally to the face of the optical inlet slit, that is, from the narrow side of the throttled portion, and the luminescence emitted from the living cells is received from the optical inlet slit, that is, rectangularly to the irradiation.

The use of a conventional photomultiplier for receiving the fluorescence from the detection cell may require an additional means, such as, mechanism for scanning the detection area of the photometric cell because of its large width. Therefore, the present invention provides for a contrivance in this respect, which comprises a linear slit as the optical inlet aperture for the photosensors, disposed in such a way, that it covers the entire width of the flat detection portion of the detection cell and faces closely to the flat face of the detection portion, a condenser lens to build up an image of the luminous points appearing in the detection area of the detection cell and a plurality of photosensors arranged in a row parallel to the inlet slit in such a manner, that the image of the luminous points formed by the condenser lens will be focused onto this row of photosensors.

By the method for counting living microbes according to the present invention, it is now possible to attain a continuous real time counting of existing microbes in a large amount of a liquid sample through its entire volume, since the microbe cells are counted as individual luminous spots in a continuously flowing sample.

As to a reagent which can be employed in accordance with the present invention for causing a reaction with one or more substances intrinsic to the living microbe cell to form a fluorescent product within the living cell, the inventors have determined that fluorescein diacetate (abbreviated hereinafter as FDA) was suitable. The reaction of FDA with a cyto-intrinsic substance, such as hydrolase, may be indicated schematically as follows:

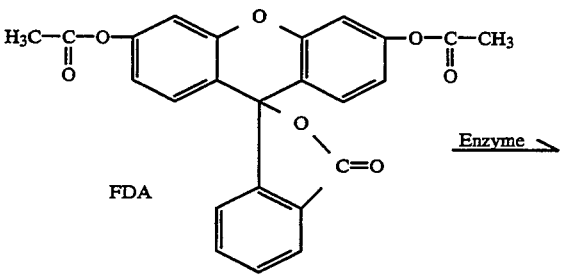

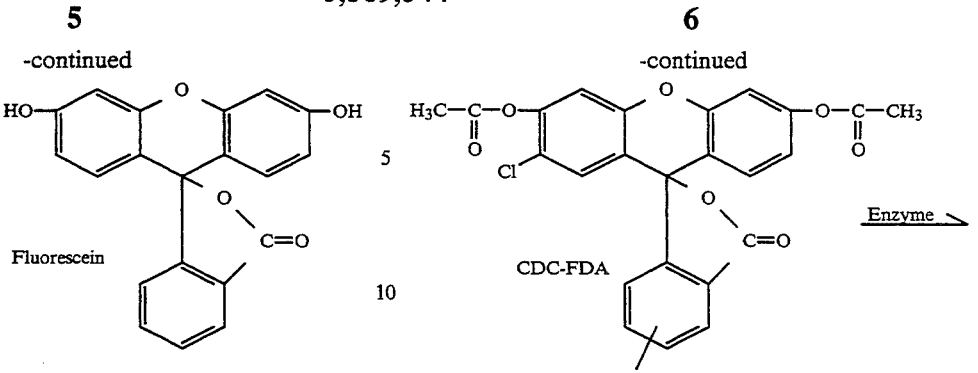

Fluorescein

While FDA as shown, capable of reacting with the cyto-intrinsic substance to form an accumulative fluorescent product within the living cell according to the present invention, problems arose using FDA. Deposition of FDA occurred on the wall surfaces of the detection cell and of the sample flow line during a prolonged continuous operation of the apparatus, thereby obstructing clear detection of the fluorescence from individual microbial cells. Also FDA fragments exfoliated from such wall surfaces would have caused detection error, requiring the need of frequent cleaning of the flow line and detection cell.

Consequently the inventors looked for other reagents which do not show the difficulties mentioned above and can be replaced for FDA. It was discovered that use of 5-carboxyfluorescein diacetate and/or 6-carboxyfluorescein diacetate (hereinafter denoted both as C—FDA) or 5-carboxy-2',7'-dichlorofluorescein diacetate and/or 6-carboxy-2',7'-dichlorofluorescein diacetate (hereinafter denoted both as CDC—FDA) is highly preferable in this respect.

C—FDA and CDC—FDA themselves do not reveal any fluorescence but will form each a fluorescent product of 5-carboxyfluorescein, 6-carboxyfluorescein, 5-carboxy-2',7'-dichlorofluorescein or 6-carboxy-2', 7'-dichlorofluorescein, respectively, upon reaction with enzymes present in the living microbial cells, above all, esterases. These fluorescent products are accumulated within the living cell.

The enzymatic reactions of C—FDA and CDC—FDA may be illustrated schematically as follows:

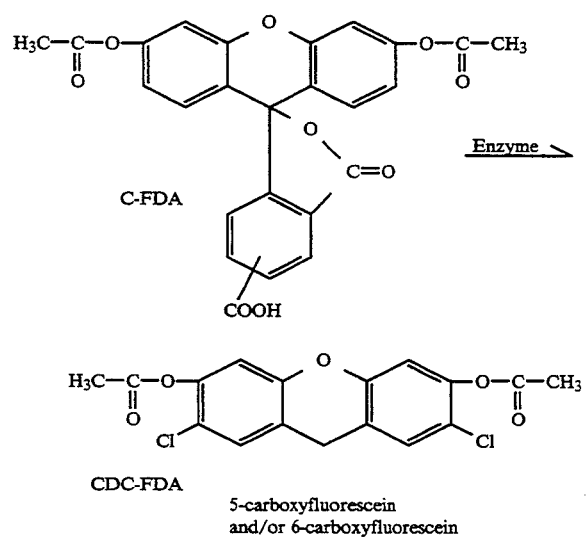

5-carboxyfluorescein and/or 6-carboxyfluorescein

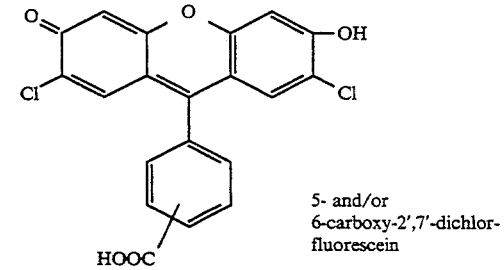

5- and/or 6-carboxy-2',7'-dichlorofluorescein

The C—FDA and CDC—FDA have solubilities in water of at least 100 µg/ml. In the practice, the rate of addition of them to the flowing sample amounts usually to 50 -100 µg/ml, which is well below the solubility limit of these reagents in water. Thus any problem of deposition onto the inside surfaces of the apparatus, such as, detection cell, supply line etc., is excluded.

It should also be pointed out, that the problem of deposition of FDA on the internal surfaces of the apparatus is, as clarified by the inventors, due to the extremely low solubility of FDA in water, which is below 1µg/ml. Thus, becoming micronous deposits on internal surfaces of the apparatus which grow gradually during prolonged successive operation of the apparatus until a cleaning thereof becomes necessary.

Upon irradiation of the living microbial cells containing the accumulated fluorescent product, a fluorescence is emitted from the living cell and the individual microbial cells become detectable as luminous points. Dead cells can produce no fluorescent product due to deactivation of the enzymes. Thus, only living cells are counted by the method according to the present invention.

With the present invention, it is now possible to count living microbial cells in various raw materials, materials of production and so on, within a few minutes, even in a sample of low microbe population, as contrasted to the prior technique in which only analogue determination has been possible with considerable time consumption of, such as, one to several days. Furthermore, method of the present invention enables dealing with a large number of samples by designing the elements of the apparatus, such as, the detection cell, irradiation means, photometric detection system and so on, in a suitable construction, size and configuration. By the technique according to the present invention, a real time assessment and control of product quality, pasteurization effect and so on may be realized.

BRIEF DESCRIPTION OF THE DRAWINGS

FIGS. 1 (a)–1(c) serve for explanation of a typical apparatus for realizing the technique according to the present invention, in which

DETAILED DESCRIPTION OF THE PREFERRED EMBODIMENTS

EXAMPLE 1

Figure 1A:
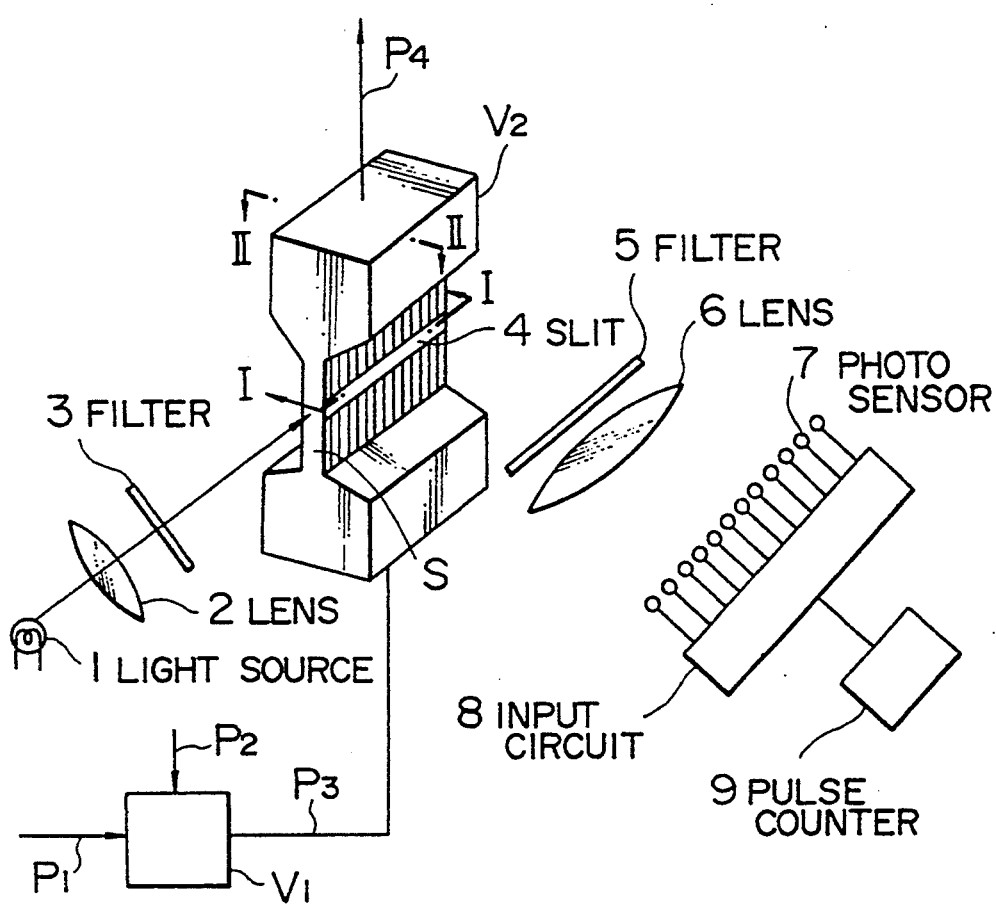
FIG. 1(a) is an explanatory perspective view of essential construction of the apparatus.
Figure 1B:
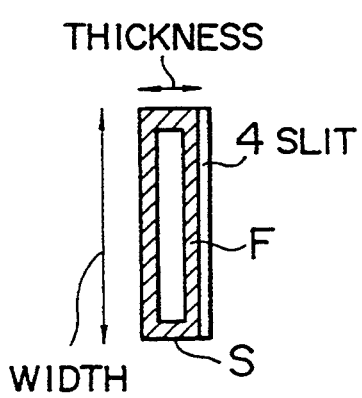
FIG. 1(b) is a section through the plane I—I of FIG. 1(a) and FIG. 1(c) is a section through the plane II—II of FIG. 1(a).
Figure 1C:
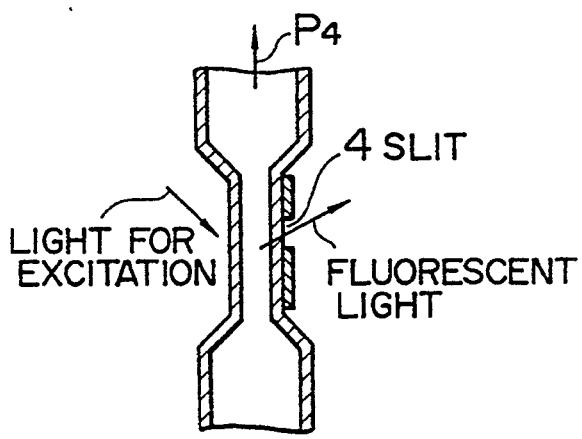

One embodiment of the present invention is explained below with reference to FIGS. 1(a)-(c). A sample to be examined for the microbe population is supplied to a reactor $V_1$ via a line $P_1$. To the reactor $V_1$ is also supplied a solution of FDA in acetone from line $P_2$. The mixture of FDA and the sample is maintained in the reactor $V_1$ for a definite residence time at a definite temperature, whereupon the mixture is introduced into a photometric detection cell $V_2$ and is examined for any existence of fluorescent microbe cells.

While the residence time in the reactor, namely the reaction time, and the concentration of FDA supplied may vary depending on each specific microbe to be detected, there may be employed preferably a reaction time of 5 -10 minutes and a concentration of FDA of 50 -100 μg/ml for yeast and a reaction time of 10 -20 minutes and a concentration of FDA of 100 -150 μg/ml for Escherichia coli and for *Bacillus subtilis*. In general a reaction temperature of 30°-37° C. may be adequate. At temperatures below 10° C. or above 45° C., the reaction of FDA with the enzymes in the living microbe will produce difficulties occur and the counting of living microbes will be unsuccessful.

The fluorescence-providing reaction of FDA proceeds only in living microbe cells existing in the sample and the resulting fluorescent product, i.e. fluorescein, is accumulated within the living cell. The so treated sample is then supplied to the detection cell $V_2$, where it is irradiated with an exciting light from the light source 1 via a condenser lens 2 through a filter 3 to cause emission of fluorescence from the possibly formed fluorescein. As the light source, a mercury-arc lamp is employed. The filter 3 allows to transmit the light in the wave length range from 450–490 nm. Other light source than mercury-arc lamp can be employed so long as it emits light of wave length of 450 –490 nm effective for exciting fluorescein.

Irradiation of the sample flowing inside the detection cell $V_2$ is effected at its throttled flat portion laterally to the direction of observation of the sample for the photometric detection, i.e. at a right angle to the observation face of the cell $V_2$ through the thin side face S. Facing the wide observation face F of the cell $V_2$, a slit 4 which extends over the entire width of the cell $V_2$ as an optical inlet aperture for an optoelectronic detection unit is disposed at the portion irradiated by the exciting light. While choice of optimum slit width may depend on the microbe to be detected, a width of about 50 μm may be preferable for detecting yeast.

The detection cell $V_2$ employed had a Geometry of internal thin flow section of the throttled flat portion of 100 μm for the width of side face and 500 μm for the width of wide observation face. Both the upper and lower portions of the detection cell $V_2$ have enlarged dimensions to allow easy flow of the sample or cleaning solution.

The spectrum of fluorescence emitted from the living microbe cells has a peak at around 512 nm. Therefore a fluorescence filter 5 allowing light of wave length over 510 nm to pass therethrough and blocking up the exciting light of wave length of 450–490 nm is inserted in the light path of the detection unit subsequent to the slit 4.

The fluorescence emitted from each individual living cell is detected by means of an optoelectronic unit according to the present invention. Thus, the fluorescence is collected through the slit 4, the fluorescence filter 5 and a condenser lens 6 onto a row of a plurality of photosensors 7 aligned on a straight line and associated with a photoelectric circuit 8 to Generate an electric pulse, which is supplied to a pulse counter 9 where the pulses corresponding to the living cells are counted. While the number of photosensors may vary for each specific purpose, a photodiode array having 10 photosensors was employed for detecting yeast cells.

EXAMPLE 2

Figure 2:
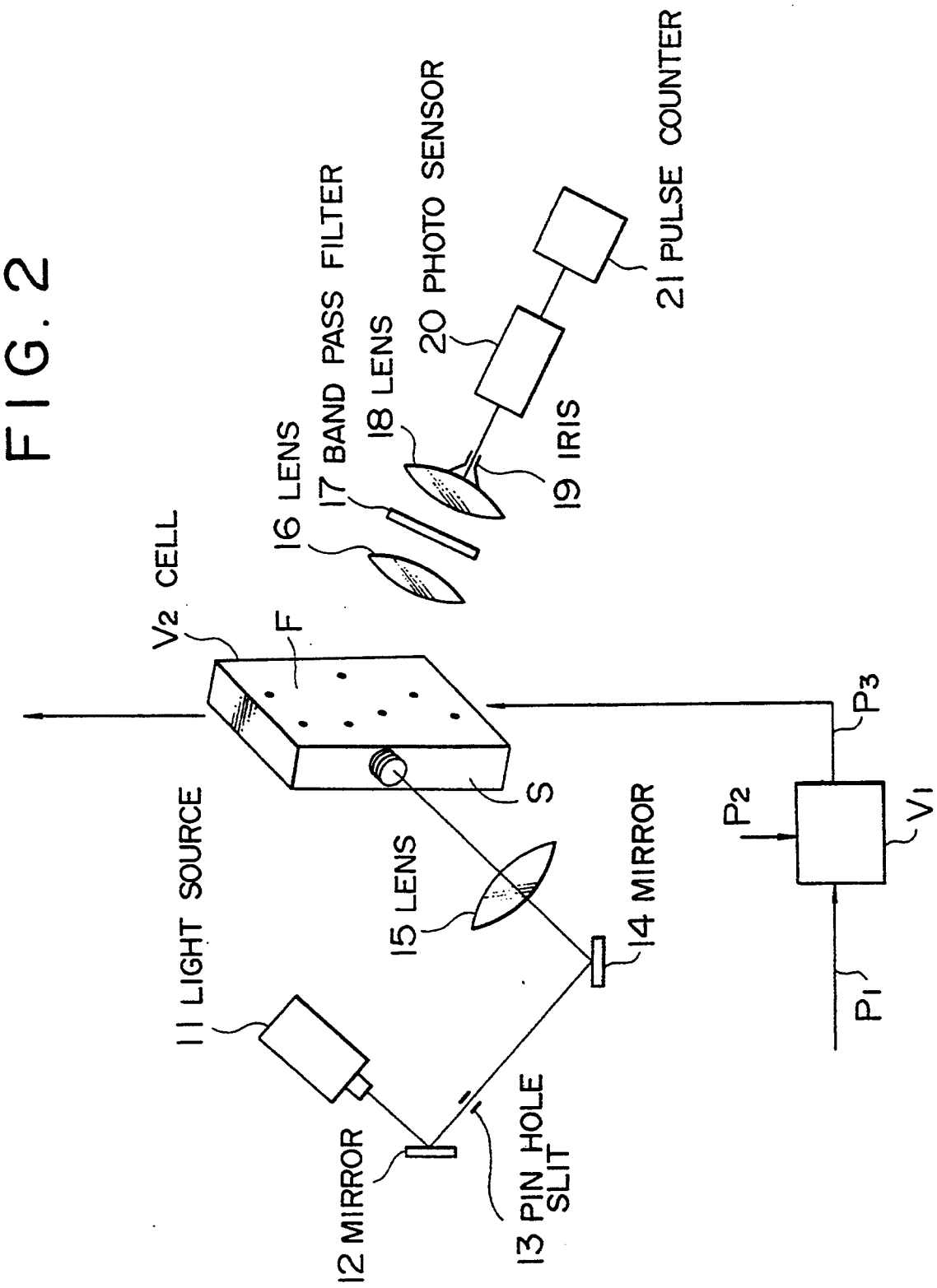
FIG. 2 is a further explanatory illustration of another embodiment of the apparatus according to the present invention.

An experiment of counting of living microbe cells was carried out using C—FDA as the reagent. This experiment is described below with reference to FIG. 2.

The liquid sample to be examined for the living microbe population was supplied to the reactor $V_1$ via a supply line $P_1$, while a solution of C—FDA in acetone having a concentration of 1 m g/ml is introduced therein via a line $P_2$. The rate of addition of the reagent solution preferably is in the range from 1/10 to 1/20 in volume ratio to the sample (this corresponds to an addition concentration of about 50 –100 μg/ml).

The mixture of the sample and C—FDA is held in the reactor $V_1$ at a predetermined temperature for a definite time, before it is supplied to the photometric detection cell $V_2$ via a supply line $P_3$.

The liquid sample had a pre-adjusted microbe population of about $10^3$ cells per milliliter of yeast. The mixture of the sample and C—FDA was maintained in the reactor $V_1$ for 5 minutes at 37° C. By the reaction of C—FDA with enzymes present in living cell of yeast, a fluorescent product is formed in the living cells of yeast, which consists of 5-carboxyfluorescein and/or 6-carboxyfluorescein, and is accumulated in the cells of yeast.

Figure 3:
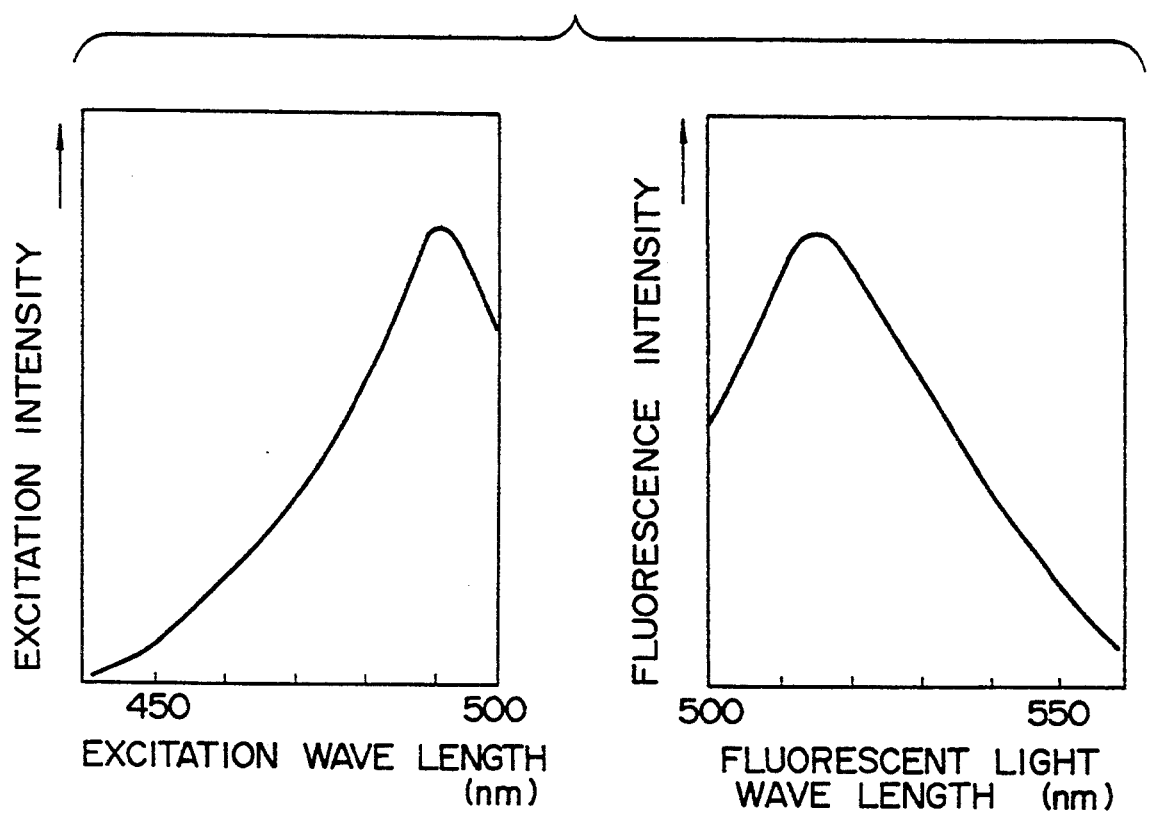
FIG. 3 includes two graphs showing each a wave-dependence of excitation or fluorescence emission for the fluorescent reaction product of C—FDA with enzymes of yeast.

FIG. 3 includes two charts showing dependence of relative excitation performance, on the one hand, and relative strength of fluorescence emission, on the other hand, on wave length. As is seen, the maximum performance for excitation of the fluorescent product is found at around a wave length of 490 nm and the maximum relative strength of fluorescence emission at around a wave length of 515 nm.

For the light source 11, an argon laser with an output power of 1 mW was employed, since its wave length 488 nm is quite near the wave length for the maximum excitation performance of 490 nm. The laser beam is projected onto the sample flowing through the detection cell $V_2$ via a mirror 12, a scattering light removing pin-hole slit 13, a deflection mirror 14 and a condenser lens 15. The living yeast cells having accumulated therein 5- and/or 6-carboxyfluorescein emit corresponding fluorescence by excitation.

The fluorescence from each individual living cell is collected by a set of condenser lenses 16, 18 and is focussed onto the photosensor 20 consisting of a photomultiplier. The electric pulse produced and amplified in the photosensor 20 is fed to a pulse counter 21 consisting of a photon counter whereby the living cells in the sample are counted as each electric pulse.

For avoiding any counting error from extraneous light, a band-pass filter 17 permitting transmission of only a light of wave length around 515 nm (i.e. the wave length of maximum fluorescence emission) is inserted between the condenser lenses 16 and 18.

The photometric detection cell $V_2$ had a geometry of its internal thin flow section of 0.1 cm width, 0.01 cm thickness and 5 cm height. The exciting light is projected onto the thin flow section at its face S of thickness and the fluorescence emitted from the flowing sample is detected from the face F of width thereof. The flow velocity of the sample inside the detection cell $V_2$ was settled at 1 cm/sec.

Figure 4:
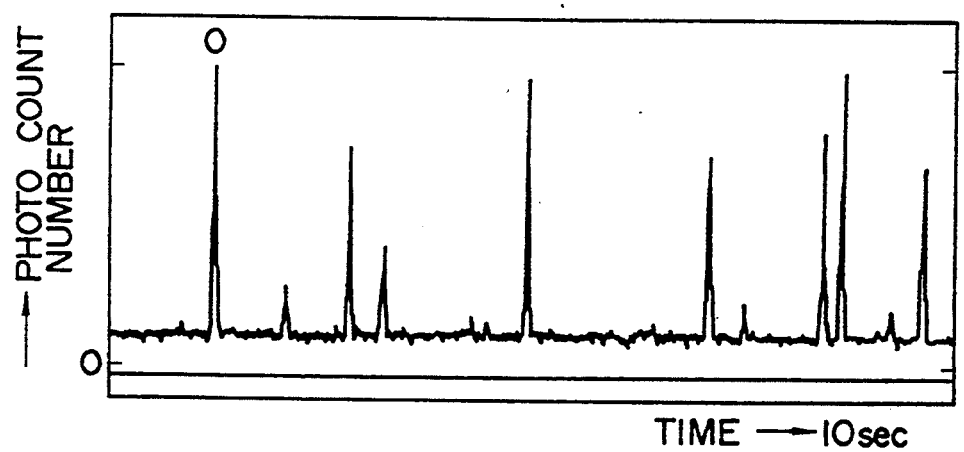
FIG. 4 is a pulse-time chart for counting pulses during a determined time interval resulting from Example 2.

FIG. 4 shows the pulse-time chart obtained in this experiment, in which strength of each electric pulse as number of photon count (ordinate) is plotted over a time interval (abscissa).

The flow rate of the sample is calculated from the flow sectional area ($0.1 \times 0.01 = 0.001$ cm$^2$) and the flow velocity (1 cm/sec) to be 0.001 cm$^3$/sec. Thus, a volume of 0.01 cm$^3$ of the sample passes the detection area per 10 seconds. FIG. 4 indicates that 11 cells had passed the detection area per 10 seconds, so that 11 cells were contained in 0.01 cm$^3$ of the sample. This figure corresponds to $1.1 \times 10^3$ cells per milliliter of the sample, which is close to the pre-adjusted actual value of $1 \times 10^3$.

In addition, it is pointed out that a continuous detection of the living cells using FDA under the same experimental condition with the case of using C—FDA operated well until about 10 minutes from the start of running, but became difficult then due to occurrence of deposition of FDA on the cell internal surface. On the contrary, use of C—FDA did not cause such trouble of deposition, and the continuous operation succeeded even after 10 hours and more.

EXAMPLE 3

The experiment of Example 2 was repeated with only exception that the reagent C—FDA was replaced by CDC—FDA. Experimental results corresponded to those of example 2.

We claim:

1. A method of continuously counting only living microbial cells in a fluid sample, comprising the steps of:
    a) adding to the sample a reagent capable of reacting with at least one enzyme of the living cells to form an accumulative fluorescent product within the living cells, said reagent being at least one derivative of fluorescein selected from the group consisting of 5-carboxyfluorescein diacetate and 6-carboxyfluorescein diacetate;
    b) continuously passing the sample from step (a) through a photometric detection cell while irradiating the sample with a light having a wavelength in a range of 450–490 nm to induce excitation of the fluorescent product accumulated within each of the living cells, thereby causing emission of a corresponding fluorescence from each of the living cells as an individual luminous point; and
    c) counting up the individual luminous points appearing within a detection area in a certain time interval with a plurality of photosensors.

2. A method of continuously counting only living microbial cells in a fluid sample, comprising the steps of:
    a) adding to the sample a reagent capable of reacting with at least one enzyme of the living cells to form an accumulative fluorescent product within the living cells, said reagent being at least one derivative of fluorescein selected from the group consisting of 5-carboxy-2',7'-dichlorofluorescein diacetate and 6-carboxy-2',7'-dichlorofluorescein diacetate;
    b) continuously passing the sample from step (a) through a photometric detection cell while irradiating the sample with a light having a wavelength in a range of 450–490 nm to induce excitation of the fluorescent product accumulated within each of the living cells, thereby causing emission of a corresponding fluorescence from each of the living cells as an individual luminous point; and
    c) counting up the individual luminous points appearing within a detection area in a certain time interval with a plurality of photosensors.

* * * * *